United States Patent [19]

Petersen et al.

[11] 4,005,096
[45] Jan. 25, 1977

[54] THERAPEUTICALLY ACTIVE PHENOXYALKYLAMINES

[75] Inventors: Rudolf Theodor Petersen, Wohltorf; Wolfgang Fleck, Hamburg, both of Germany

[73] Assignee: Biersdorf Aktiengesellschaft, Hamburg, Germany

[22] Filed: Feb. 25, 1976

[21] Appl. No.: 661,156

Related U.S. Application Data

[62] Division of Ser. No. 532,673, Dec. 13, 1974, Pat. No. 3,960,878.

[30] Foreign Application Priority Data

Dec. 27, 1973 Germany .................... 2364685

[52] U.S. Cl. .............. 260/294.9; 260/296 AE; 424/263
[51] Int. Cl.² ................................ C07D 213/38
[58] Field of Search ............... 260/294.9, 296 AE

[56] References Cited

FOREIGN PATENTS OR APPLICATIONS 650,560   10/1962   Canada ............. 260/296 AE Primary Examiner—John D. Randolph
Attorney, Agent, or Firm—Stevens, Davis, Miller & Mosher

[57] ABSTRACT

Compounds of the formula:

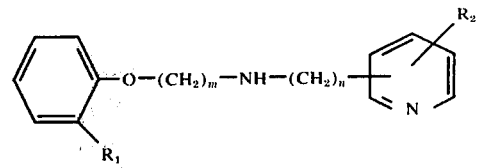

(wherein
$R_1$ represents a chlorine atom or a methoxy or cyano group;
$R_2$ represents a hydrogen atom or a methyl or hydroxy group;
$m$ is 2, 3 or 4; and
$n$ is 1 or 2)

and their physiologically acceptable acid addition salts have blood pressure reducing properties and may be used in the treatment of patients.

3 Claims, No Drawings

THERAPEUTICALLY ACTIVE PHENOXYALKYLAMINES

This is a continuation division of application Ser. No. 532,673 filed Dec. 13, 1974, now U.S. Pat. No. 3,960,878 granted June 1, 1976.

This invention relates to therapeutically active phenoxyalkylamines.

According to the present invention there are provided compounds of the formula I:

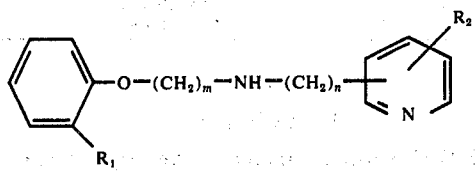

wherein
$R_1$ represents a chlorine atom or a methoxy or cyano group;
$R_2$ represents a hydrogen atom or a methyl or hydroxy group;
$m$ is 2, 3 or 4; and
$n$ is 1 or 2 and their physiologically acceptable acid addition salts.

The compounds of formula I and their physiologically acceptable acid addition salts have valuable pharmacological properties. In particular they have blood pressure reducing properties and generate, after administration to rats with artificially promoted high pressure, a marked diminution in blood pressure of long duration. They may be administered perorally. Further they are of low toxicity. They are therefore suitable as therapeutic agents particularly for treating cronic high blood pressure. The compounds of formula I can be used as such but are preferably used in the form of their good crystallising acid addition salts.

Compounds of formula I (including their physiologically acceptable acid addition salts) which may be mentioned include N-[4-Pyridyl-ethyl(2)]-o-methoxy-phenoxyethylamine; N-[2-Pyridyl-ethyl(2)]-o-methoxy-phenoxyethylamine; N-(3-Pyridyl-methyl)-o-methoxy-phenoxyethylamine; N-(2-Pyridyl-methyl)-o-methoxy-phenoxyethylamine; N-(4-Pyridyl-methyl)-o-methoxy-phenoxyethylamine; N-[4-Pyridyl-ethyl (2)]-o-chloro-phenoxypropylamine; N-[4-Pyridyl-ethyl (2)]-o-chloro-phenoxyethylamine; N-[(3-Methyl-2-pyridyl)-methyl]-o-chloro-phenoxyethylamine; N-[(3-Methyl-2-pyridyl)-methyl]-o-cyano-phenoxyethylamine; N-[4-Pyridyl-ethyl (2) ]-o-chloro-phenoxybutylamine; N-[4-Pyridyl-ethyl (2)]-o-cyano-phenoxyethylamine; and N-[(3-Hydroxy-2-pyridyl)-methyl]-o-methoxy-phenoxyethylamine.

The compounds of formula I wherein $n$ is 2 may be prepared in known manner by reaction of a compound of the formula II:

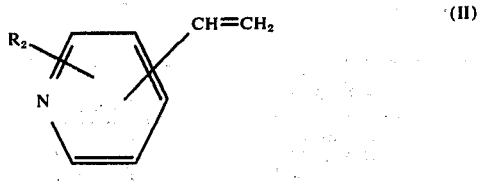

(in which $R_2$ is as defined above) with a compound of the formula III:

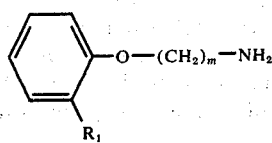

(wherein $R_1$ and $m$ are as defined above).

This reaction of compounds of formula II with compounds of formula III is preferably performed in a lower alcohol, such as methanol, and preferably in the presence of glacial acetic acid with several hours refluxing. The molecular ratio of the reactants is suitably 1:1. The reaction time depends upon the reactant chosen but is generally about 3 to 8 hours.

Compounds of formula I wherein $n$ is 1 may be prepared in known manner by reacting, with or without an organic solvent, a compound of the formula IV:

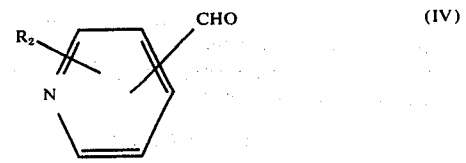

(wherein $R_2$ is as defined above) with a compound of formula III to form a Schiff's base and reducing the Schiff's base, without isolation, with a reducing agent.

The reaction of the compound of formula IV with the compound of formula III to form the Schiff's base may be carried out, in the absence of solvent, by heating a mixture of the two reactants in a molecular ratio of about 1:1 for about 1 hour at a temperature of about 90° to 110° C. When a solvent is used, it is preferably a water-immiscible solvent such as e.g. toluene. The reaction is then carried out by heating under reflux for several hours. A reducing agent is added to the reaction mixture after cooling but without isolating the Schiff's base formed as an intermediary and, if one is working without solvent, an organic solvent is also added. Then the mixture is stirred for about half an hour at room temperature and then heated for several hours to reduce the Schiff's base to the desired secondary amine of formula I. As reducing agent there are suitable Raney catalysts and metal hydrides particularly sodium borohydride.

The isolation of the reaction product may be carried out in known manner. If desired the free base of formula I may be converted into a physiologically acceptable acid addition salt by reaction with an acid. The good crystallising acid addition salts (e.g. hydrochloride, oxalate and maleinate) can be prepared from the isolated bases, which often precipitate as oily products, in known manner e.g. by dissolution in ethanol and precipitation with acids such as hydrochloric acid, oxalic acid or maleic acid, and these can be further purified by recrystallisation. Also if desired the purified salts can be reconverted in known matter, e.g. by reaction with a basic material, back into a free base.

The starting pyridine derivatives of formula II and IV are generally known compounds described in the literature but, if new, they may be prepared by known methods. Thus compounds of formula II (vinylpyridines)

may be prepared by splitting water off from a β-hydroxyethylpyridine. The latter may be obtained by condensation of a picoline with formaldehyde (L. and M. Fieser, "Organic Chemistry," Verlag Chemie, Weinheim, 1965, page 1452). Compounds of general formula IV (pyridinealdehydes) may be obtained by oxidation in an air stream of picolines with the aid of catalysts (L. and M. Fieser, "Organic Chemistry", 1965, page 1446).

The primary amines of formula III may be prepared from the corresponding phenols by converting these into phenoxyalkylbromides by reaction with ethylene bromide and then converting the phenoxyalkylbromides into the amines of formula III by the phthalimide splitting route according to Gabriel.

The invention also provides pharmaceutical compositions which comprise a compound of formula I or a physiologically acceptable acid addition salt thereof together with a pharmacologically acceptable carrier or diluent. The compositions may be solid or liquid. The compositions may be in the form for example, of injectable solutions and, in particular for oral administration, of pharmaceutical preparations such as dragees, pills and tablets.

The invention is further illustrated by way of example in the following Examples.

EXAMPLE 1

N-[4-Pyridyl-ethyl(2)]-o-methoxy-phenoxyethylamine.2 HCl (Compound A)

8.3 g (0.05 mol) o-Methoxy-phenoxyethylamine and 5.3 g (0.05 mol) 4-vinylpyridine were dissolved in 25 ml methanol and then 3.0 g (0.05 mol) glacial acetic acid were added. The mixture was refluxed for 8 hours. After evaporation of the solvent in a rotary evaporator the remaining syrup was made alkaline with aqueous sodium carbonate solution and extracted several times with chloroform. The organic phase was dried with anhydrous potassium carbonate and the chloroform evaporated off. The residue was dissolved in about 30 ml ethanol and acidified with ethereal hydrochloric acid. After the addition of diethyl ether until cloudiness appeared, the product slowly crystallised out. It was recrystallised once from ethanol and diethyl ether.

| Mp. 198 – 201° C | Yield: 29% | Analysis for $C_{16}H_{22}Cl_2N_2O$ |
|---|---|---|
| Calculated: | | Found: |
| C = 55.66% | | C = 55.35% |
| H = 6.42% | | H = 6.38% |
| Cl = 20.54% | | Cl = 20.07% |
| N = 8.11% | | N = 7.69% |

EXAMPLE 2

N-[2-Pyridyl-ethyl(2)]-o-methoxy-phenoxyethylamine . 2 HCl (Compound B)

The quantities of reactants and the reaction conditions corresponded to those in Example 1. In place of 4-vinylpyridine 2-vinylpyridine was used. To the residue obtained after evaporating the chloroform there was added ethanolic maleic acid. The maleinate, with a melting point of 99° – 100° C, crystallised out after which it was recrystallised once from ethanol and diethyl ether.

Yield: 43.5%

After conversation into the free base, the hydrochloride can also be prepared using ethanolic hydrochloric acid in which case it crystallises out with ½ $H_2O$.

| Mp. 49 to 50° C | Analysis for: | $C_{16}H_{22}Cl_2N_2O_2$ |
|---|---|---|
| Calculated: | | Found: |
| C = 54.24% | | C = 54.14% |
| H = 6.54% | | H = 6.30% |
| Cl = 20.02% | | Cl = 20.32% |
| N = 7.91% | | N = 7.55% |

EXAMPLE 3

N-(3-Pyridyl-methyl)-o-methoxy-phenoxyethylamine .2 HCl (Compound C)

10 g (0.06 mol) o-Methoxy-phenoxyethylamine were mixed with 6.4 g (0.06 mol) pyridine-3-aldehyde, heated to 105° C and kept at this temperature for 3 hours. The cooled mixture was dissolved in 400 ml methanol. The solution was cooled to 5° C and 5.7 g (0.15 mol) sodium borohydride added in small portions. The mixture was stirred for half an hour at room temperature and then refluxed for 6 hours.

The solvent was distilled off in vacuo and the residue taken up in dilute hydrochloric acid. After shaking of the acid phase with diethyl ether, it was made alkaline with aqueous potassium carbonate solution and the base taken up in diethyl ether. After drying with potassium carbonate and evaporation of the ether, the residue was taken up in ethanol and acidified with ethereal hydrochloric acid. White crystals precipitated which were recrystallised twice from ethanol and diethyl ether. They had a melting point of 152° to 155° C and were hygroscopic.

| Yield: 22% | |
|---|---|
| Calculated | Found: |
| C = 54.39% | C = 54.70% |
| H = 6.09% | H = 5.95% |
| Cl = 21.40% | Cl = 21.03% |
| N = 8.46% | N = 8.12% |

EXAMPLE 4

N-(2-Pyridyl-methyl)-o-methoxy-phenoxyethylamine. 2 HCl (Compound D)

The amounts used and conditions were as in Example 3. In place of the pyridine-3-aldehyde pyridine-2-aldehyde was used. The dihydrochloride was not hygroscopic and had to be recrystallised many times from ethanol/diethyl ether before the melting point remained constant at 177° – 179° C.

| Yield: 25% | |
|---|---|
| Calculated: | Found: |
| C = 54.39% | C = 54.12% |
| H = 6.09% | H = 6.05% |
| Cl = 21.40% | Cl = 20.93% |

-continued

| Yield: 25% | |
|---|---|
| Calculated: | Found: |
| N = 8.46% | N = 8.40% |

EXAMPLE 5

N-(4-Pyridyl-methyl)-o-methoxy-phenoxyethylamine . 2 HCl (Compound E)

Amounts of materials and conditions were chosen as in Example 3. In place of pyridine-3-aldehyde pyridine-4-aldehyde was used. After twice recrystallising the dihydrochloride from ethanol/diethyl ether the melting point was 178° – 179° C.

| Yield: 66% | Analysis for: | $C_{15}H_{20}Cl_2N_2O_2$ |
|---|---|---|
| | Calculated: | Found: |
| | C = 54.39% | C = 54.84% |
| | H = 6.09% | H = 5.97% |
| | Cl = 21.40% | Cl = 21.30% |
| | N = 8.46% | N = 8.30% |

EXAMPLE 6

N-[4-Pyridyl-ethyl(2)]-o-chloro-phenoxypropylamine dioxalate dihydrate (Compound F)

27.2 g (0.1465 mol) o-Chloro-phenoxypropylamine and 15.5 g (0.1465 mol) 4-vinylpyridine were dissolved in 73 ml methanol and then 8.8 g (0.1465 mol) glacial acetic acid was added thereto. Thereafter the mixture was heated for 8 hours under reflux. After evaporating off the solvent in a rotary evaporator, the remaining residue was taken up in sodium carbonate solution and extracted many times with chloroform. The organic phase was dried with anhydrous magnesium sulphate and the chloroform was evaporated off. The residue was dissolved in 100 ml methanol and methanolic oxalic acid was added until an acid reaction took place. The precipitated crystals were recrystallised from methanol/water (50:50).

| Mp. 164 – 165° C | Yield: 46% |
|---|---|
| Calculated: | Found: |
| C = 47.35% | C = 47.43% |
| H = 5.36% | H = 5.26% |
| Cl = 7.00% | Cl = 6.97% |
| N = 5.52% | N = 5.49% |

EXAMPLE 7

N-[4-Pyridyl-ethyl(2)]-o-chloro-phenoxyethylamine dioxalate dihydrate (Compound G)

12.2 g (0.071 mol) o-Chloro-phenoxyethylamine and 7.5 g (0.071 mol) 4-vinylpyridine were dissolved in 36 ml methanol and then 4.25 g (0.071 mol) glacial acetic acid were added. The mixture was heated for 8 hours under reflux. After evaporating off the solvent in a rotary evaporator the residue was taken up in sodium carbonate solution and extracted many times with chloroform. The organic phase was dried with anhydrous magnesium sulphate and the chloroform was evaporated off. The residue was dissolved in 70 ml methanol and treated with methanolic oxalic acid. The precipitated crystals were recrystallised from water.

| Mp. 170° C | Yield: 57% |
|---|---|
| Calculated: | Found: |
| C = 46.31% | C = 46.05% |
| H = 5.12% | H = 4.87% |
| Cl = 7.20% | Cl = 6.88% |
| N = 5.68% | N = 5.63% |

EXAMPLE 8

N-[(3-Methyl-2-pyridyl)-methyl]-o-chloro-phenoxyethylamineoxalate hydrate (Compound H)

8.6 g (0.05 mol) o-Chloro-phenoxyethylamine and 6.1 g (0.05 mol) 6-methylpyridine-2-aldehyde were heated for 1 hour to 90° C. The cooled reaction mixture was taken up in 330 ml methanol and cooled to 0° C. Then to the solution there was added 4.8 g (0.125 mol) sodium borohydride in small portions. After the addition was complete the mixture was stirred for half an hour at room temperature and then refluxed for 5 hours. The solvent was dissolved off in vacuo and the residue taken up in 2N-hydrochloric acid. The acidic aqueous phase was shaken with chloroform and then made alkaline with sodium carbonate solution. The free base was extracted with chloroform. After drying with anhydrous magnesium sulphate the solvent was distilled off and the residue dissolved in 80 ml ethanol. After the addition of methanolic oxalic acid, crystals precipitated which were recrystallised from methanol.

| M.p. 164 – 166° C | Yield: 37% |
|---|---|
| Calculated: | Found: |
| C = 54.40% | C = 54.01% |
| H = 5.33% | H = 4.92% |
| Cl = 9.46% | Cl = 9.31% |
| N = 7.45% | N = 7.46% |

EXAMPLE 9

N-[(3-Methyl-2-pyridyl)-methyl]-o-cyano-phenoxyethylamineoxalate hydrate (Compound J)

7.5 g (0.045 mol) o-Cyano-phenoxyethylamine and 5.5, (0.045 mol) 6-methyl-pyridine-2-aldehyde were heated for 1 hour to 90° C.

The reactions conditions were as in Example 8.

| Mp. 192° C | Yield: 29% |
|---|---|
| Calculated: | Found: |
| C = 58.90% | C = 58.80% |
| H = 5.18% | H = 5.34% |
| N = 11.40% | H = 11.33% |

EXAMPLE 10

N-[4-Pyridyl-ethyl(2)]-o-chloro-phenoxybutylamine dioxalate monohydrate (Compound K)

10.0 g (0.05 mol) o-Chloro-phenoxybutylamine and 5.3 g (0.05 mol) 4-vinylpyridine were dissolved in 25 ml methanol and then 3.0 g (0.05 mol) glacial acetic acid added thereto. The mixture was refluxed for 8 hours.

Reaction conditions were chosen as in Example 7.

| Mp.151 – 153° C | Yield: 30% |
|---|---|
| Calculated: | Found: |
| C = 48.43% | C = 48.99% |
| H = 5.57% | H = 5.12% |
| Cl = 6.83% | Cl = 6.86% |
| N = 5.38% | N = 5.07% |

EXAMPLE 11

N-[4-Pyridyl-ethyl(2)]-o-cyano-phenoxyethylamine dioxalate hydrate (Compound L)

7.5 g (0.045 mol) o-Cyano-phenoxyethylamine and 4.75 g (0.045 mol) 4-vinylpyridine were dissolved in 25 ml methanol and then 2.7 g (0.045 mol) glacial acetic acid were added thereto. The mixture was refluxed for 8 hours. The reaction conditions were as in Example 7.

| Mp. 151 – 153° C | Yield: 25% |
|---|---|
| Calculated: | Found: |
| C = 51.20% | C = 51.40% |
| H = 4.35% | H = 4.96% |
| N = 8.55% | N = 8.95% |

EXAMPLE 12

N-[(3-Hydroxy-2-pyridyl)-methyl]-o-methoxy-phenoxyethylamine dihydrochloride (Compound M)

5.5 g (0.035 mol) o-Methoxy-phenoxyethylamine and 5.85 g (0.035 mol) 3-hydroxy-pyridine-2-aldehyde were heated for 1 hour at 90° C. The cooled reaction mixture was dissolved in 250 ml methanol and cooled to 0° C. Then to the solution there was added 3.3 g (0.087 mol) sodium borohydride in small portions. The mixture was thereafter stirred for 1 hour at room temperature and then refluxed for 4 hours. The solvent was distilled off in vacuo and the residue taken up in 2N-hydrochloric acid. The acid phase was shaken with chloroform and then made alkaline with sodium carbonate. The free base was extracted with chloroform. After drying with anhydrous magnesium sulphate the solvent was distilled off and the residue dissolved in 20 ml ethanol.

On the addition of ethereal hydrochloric acid, crystals precipitated which were recrystallised from isopropanol/$H_2O$ (80:20).

| Mp. 197 – 199° C | Yield: 21% |
|---|---|
| Calculated: | Found: |
| C = 51.80% | C = 52.08% |
| H = 5.80% | H = 5.97% |
| Mp. 197 – 199° C | Yield: 21% |
| Calculated: | Found: |
| Cl = 20.41% | Cl = 20.28% |
| N = 8.06% | N = 8.10%. |

To show the blood pressure reducing properties of typical compounds according to the invention, products of the Examples were administered, to rats having artificially promoted high blood pressure (according to Goldblatt), in the form of solution either by injection under the skin of the back (subcutaneously) or by means of a stomach tube (perorally). 1,2.5 and 4 hours (and 1.75 hours in the case of Compound A) after administration of the substance the systolic and diastolic blood pressures were measured plethysmographically at the base of the tail of the rat.

In the following Table I there is given for each of the individual compounds (designated A to M) the average value of the blood pressure in mm Hg before the administration of the compound, the time (determined from the measuring time) of maximum blood pressure reduction and the maximum reduction of the systolic and diastolic blood pressures expressed as a percentage of the initial value after a single administration of the dose.

Table I

| Compound | No. of animals | Dose Mg/kg body weight | Initial blood pressure (mm. Hg) | Maximum blood pressure reduction Hours after application | Percent blood pressure reduction % |
|---|---|---|---|---|---|
| A | 28 | 10 s.c. | 200/169 | 1.75 | −25/−34 |
| A | 16 | 20 p.o. | 202/167 | 1 | −28/−32 |
| B | 10 | 10 s.c. | 195/162 | 2.5 | −20/−23 |
| C | 6 | 10 s.c. | 200/165 | 1 | −15/−16 |
| D | 6 | 10 s.c. | 191/158 | 2.5 | −22/−25 |
| e | 6 | 10 s.c. | 196/153 | 4 | −15/−18 |
| E | 8 | 10 p.o. | 200/166 | 2.5 | −20/−22 |
| F | 8 | 10 s.c. | 190/157 | 1 | −16/−19 |
|  |  |  |  | 2.5 | −15/−17 |
| G | 8 | 10 s.c. | 219/185 | 1 | −17/−21 |
|  |  |  |  | 4 | −15/−16 |
| H | 9 | 10 s.c. | 216/180 | 2.5 | −16/−16 |
| J | 10 | 10 s.c. | 220/190 | 1 | −11/−12 |
| K | 10 | 10 s.c. | 207/173 | 2.5 | −15/−19 |
| L | 10 | 10 s.c. | 222/192 | 1 | −17/−19 |
| M | 6 | 10 s.c. | 231/200 | 4 | −11/−12 | s.c. = subcutaneous
p.o. = peroral

As is evident from Table I the substances according to the invention generate a marked, and in some cases continuing, reduction in blood pressure and also work with peroral administration.

As a result of tests carried out it is believed that an α-sympathicolytic component takes part in the blood pressure action. This is evident from the displacement of the dose/action curve of noradrenalin after the administration of a compound of the invention. Surprisingly however there is substantially no increase in heart frequency with some of the tested compounds despite the definite reduction in the blood pressure. This is in contrast to known α-receptor blocking agents where such an increase is always observed.

Tests to determine the toxicity have been carried out. In each case 6 mice were given a particular dose of the compound to be tested combined with a suitable neutral diluent, administration being carried out perorally, intraveneously and/or intraperitoneally.

The statistical evaluation took place according to the method of J. F. Litchfield, Jr. and F. Wilcoxon in: "Journal of Pharmacology and Experimental Therapeutics", Volume 96 (1949), pages 99–113.

In the following Table II the toxicity of Compounds A to M are given.

Table II

| Compound | Toxicity ($LD_{50}$ Mouse) mg/kg | |
| --- | --- | --- |
|   | 53.47 | i.v. |
|   | 290 | p.o. |
| A | 150 | i.p. |
|   | 31.53 | i.v. |
| B | 150 | i.p. |
|   | 73.33 | i.v. |
|   | 390 | p.o. |
| C | 150 | i.p. |
|   | 51.01 | i.v. |
|   | 750 | p.o. |
| D | 150 | i.p. |
|   | 90.07 | i.v. |
|   | 730 | p.o. |
| E | 364 | i.p. |
| F | >800 | i.p. |
|   | 71.68 | i.v. |
| G | Ω200 | i.p. |
|   | 49.95 | i.v. |
| H | 220 | i.p. |
|   | 73.33 | i.v. |
| J | 660 | p.o. |
|   | 182 | i.p. |
| K | 235 | p.o. |
|   | 245 | p.o. |
| L | 91 | i.p. |
| M | 55.64 | i.v. | p.o. = peroral
i.v. = intraveneously
i.p. = intraperitoneally

The following Examples illustrate pharmaceutical compositions according to the invention:

EXAMPLE 13

| Example 13 Composition of a tablet Components | Quantities by weight |
| --- | --- |
| N-[4-Pyridyl-ethyl(2)]-o-methoxy phenoxyethylamine dihydrochloride | 40 mg |
| Milk sugar (Lactose) | 62 mg |
| Gelatin | 1 mg |
| Formalin-Casein (Dissintegration Agent) | 4 mg |
| Stearic acid, powdered (Lubricant) | 3 mg |
|   | 110 mg |

The active substance and the greater part of the milk sugar (about ⅔ of the total quantity) were mixed and worked to a paste with a warmed solution of the gelatin in 16 mg water which was then passed in a damp condition through a sieve of 1.5 mm mesh width. The granulate so formed was dried at about 40° C and in dried condition passed again through a sieve of 1.0 mm mesh width. After the addition of the powdered stearic acid, the formalin-casein and the remaining milk sugar, the so treated granulate was then pressed to tablets using a suitable device.

EXAMPLE 14

| Example 14 Compound of an injectable solution (for 2 ml ampoules): Components | Quantities by weight |
| --- | --- |
| N-[4-Pyridyl-ethyl (2)]-o-methoxy-phenoxyethylamine dihydrochloride | 30 mg |
| "Glycofurol" (x Roche) - Ether of tetrahydrofurfurylalcohol with polyethyleneglycol 100 | 0.9 ml |
| Twice distilled water | to 2.0 ml |

The active substance was dissolved in the solubilizing agent ("Glycofurol") and treated with vigorous stirring in small portions with the twice distilled water, then filled into suitable ampoules. The ampoules were melt sealed and then sterilised at 120° C.

We claim:
1. Compounds of the formula I:

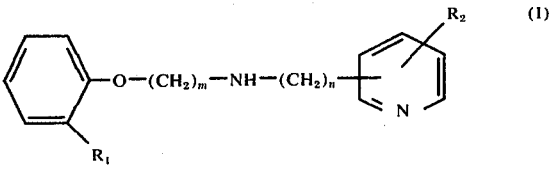

wherein
$R_1$ represents a cyano group;
$R_2$ represents a hydrogen atom or a methyl or hydroxy group;
$m$ is 2, 3 or 4; and
$n$ is 1 or 2 and their physiologically acceptable acid addition salts.

2. Compound according to claim 1 which is N-[(3-methyl-2-pyridyl)-methyl]-o-cyano-phenoxyethylamine or a physiologically acceptable acid addition salt thereof.

3. Compound according to claim 1 which is N-[4-pyridyl-ethyl (2)]-o-cyano-phenoxyethylamine or a physiologically acceptable acid addition salt thereof.

* * * * *